US012751971B2

(12) United States Patent
Peterson et al.

(10) Patent No.: US 12,751,971 B2
(45) **Date of Patent: *Oct. 6, 2026**

(54) ANTIOXIDANT AND ANTIVIRAL COMPOSITIONS AND METHODS

(71) Applicant: MAYO FOUNDATION FOR MEDICAL EDUCATION AND RESEARCH, Rochester, MN (US)

(72) Inventors: Timothy Peterson, Rochester, MN (US); Atta Behfar, Rochester, MN (US); Christopher Paradise, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1207 days.

This patent is subject to a terminal disclaimer.

(21) Appl. No.: 17/629,512

(22) PCT Filed: Jul. 23, 2020

(86) PCT No.: PCT/US2020/043305

§ 371 (c)(1),
(2) Date: Jan. 24, 2022

(87) PCT Pub. No.: WO2021/021572

PCT Pub. Date: Feb. 4, 2021

(65) Prior Publication Data

US 2022/0241325 A1 Aug. 4, 2022

Related U.S. Application Data

(60) Provisional application No. 62/879,033, filed on Jul. 26, 2019.

(51) Int. Cl.
*A61K 35/14* (2015.01)
*A61P 39/06* (2006.01)

(52) U.S. Cl.
CPC .............. *A61K 35/14* (2013.01); *A61P 39/06* (2018.01)

(58) Field of Classification Search
CPC .......... A61P 39/06; A61P 31/12; A61K 35/12; A61K 38/443
See application file for complete search history.

(56) References Cited

U.S. PATENT DOCUMENTS

| | | | | |
|---|---|---|---|---|
| 10,596,123 | B2 * | 3/2020 | Behfar | A61K 8/14 |
| 12,036,325 | B2 * | 7/2024 | Behfar | A61K 9/5089 |
| 2015/0216899 | A1 | 8/2015 | Pusic et al. | |
| 2016/0324794 | A1 * | 11/2016 | Behfar | A61K 35/16 |
| 2017/0290860 | A1 | 10/2017 | Marban et al. | |
| 2021/0169812 | A1 | 6/2021 | Behfar et al. | |

FOREIGN PATENT DOCUMENTS

| | | | | |
|---|---|---|---|---|
| WO | WO 2017/173034 | * | 10/2017 | A61K 35/12 |
| WO | WO-2017173034 A1 | * | 10/2017 | A61K 31/704 |
| WO | 2018/029656 A2 | | 2/2018 | |
| WO | WO-2019118817 A1 | * | 6/2019 | A61L 26/009 |
| WO | WO 2021/021572 A1 | | 2/2021 | |

OTHER PUBLICATIONS

Wang, W. et al., Exosomes/microvesicles from induced pluripotent stem cells deliver cardioprotective miRNAs and prevent cardiomyocyte apoptosis in the ischemic myocardium, Int J Cardiol. Aug. 1, 2015; 192: 61-69 (Year: 2015).*
Liu, Z. et al., "Exosomes from adipose-derived mesenchymal stem cells prevent cardiomyocyte apoptosis induced by oxidative stress", Cell Death Discovery (2019)5:79 (Year: 2019).*
Qi et al. "Characterization of a purified exosome product and its effects on canine flexor tenocyte biology." J Orthop Res. 2020; 38: 1845-1855.*
Wang et al. (Int J Cardiol. Aug. 1, 2015; 192: 61-69).*
Liu et al. (Cell Death Discovery (2019) 5:79).*
EP Patent Application No. 20847227.4, filed Feb. 15, 2022; European Extended Search Report issued Oct. 16, 2023, 10 pages.
EP Patent Application No. 20847227.4, filed Feb. 15, 2022; Supplementary Partial European Search Report issued Jul. 12, 2023, 10 pages.
Haney et al, "Exosomes as drug delivery vehicles for Parkinson's disease therapy," Jun. 2015, Journal of Control Release, 207:18-30.
Batrakova et al, "Using exosomes, naturally-equipped nanocarriers, for drug delivery," Dec. 2015, Journal of Control Release, 219:396-405.
Bodega et al, "Microvesicles: ROS scavengers and ROS producers," 2019, 8(1):1626654.
Hall et al, "Delivery of Therapeutic Proteins via Extracellular Vesicles: Review and Potential Treatments for Parkinson's Disease, Glioma, and Schwannoma," Mar. 2016, Cellular and Molecular Neurobiology, 36, 417-427.
PCT Patent Application No. PCT/US2020/043305, filed Jul. 23, 2020, International Search Report and Written Opinion mailed on Jan. 7, 2021; 10 pages.
PCT Patent Application No. PCT/US2020/043305, filed Jul. 23, 2020, International Preliminary Report on Patentability issued Feb. 1, 2022; 7 pages.
Igarashi et al., "Oxidative Stress Responsiveness of Cellular Senescence: Conducted by Bach1", Jun. 2009, *Biochemistry,* 81(6):502-510 (with English machine translation).

(Continued)

*Primary Examiner* — Christopher M Babic
(74) *Attorney, Agent, or Firm* — Mueting Raasch Group

(57) ABSTRACT

Preparations of exosomes and/or Purified Exosome Product (PEP) include antioxidant proteins and antiviral proteins. Compositions that include exosomes and/or PEP can be used to treat subject having, or at risk of having, a condition or tissue damage caused, at least in part, by oxidative stress. Also, compositions that include exosomes and/or PEP can be used to treat subject having, or at risk of having, a viral infection.

5 Claims, 17 Drawing Sheets

(56) References Cited

OTHER PUBLICATIONS

Matsura, "Production and Role of Oxidized Phosphatidylserine in Apoptotic Cells", 2011, *Oil Science,* 11(11):425-430 (with English machine translation).

Sekine et al., "The Reality of Diverse Cell Death", 2013, *Journal of Clinical and Experimental Medicine,* 246(5):376-382 (with English machine translation).

CA Patent Application No. 3148604, filed Jan. 24, 2022; Examiner's Report issued Oct. 9, 2025, 4 pages.

JP Patent Application No. 2022-505295, filed Jan. 24, 2022, Office Action and Pretrial Reexamination, dated Jul. 15, 2025, 9 pages (with English translation).

* cited by examiner (A)

(B)

(A)

(B)

(A) (B) (C) (D)

(E)

(A)

(B) (C) (D)

(A)

(B)

(A)

(B)

(C)

(A)

(B)

(A)

(B)

(A) (B) (C) (D) (E)

ANTIOXIDANT AND ANTIVIRAL COMPOSITIONS AND METHODS

CROSS-REFERENCE TO RELATED APPLICATION

This application is the § 371 U.S. National Stage of International Application No. PCT/US2020/043305, filed Jul. 23, 2020, which claims the benefit of U.S. Provisional Patent Application No. 62/879,033, filed Jul. 26, 2019, each of which is incorporated herein by reference in its entirety.

SUMMARY

This disclosure describes, in one aspect, a method of treating tissue damage caused by oxidative stress in a subject at risk of having tissue damage caused by oxidative stress. Generally, the method includes administering to the subject a composition that includes exosomes and/or PEP having at least one antioxidant protein in an amount effective to reduce the likelihood or severity of tissue damage compared to a subject to whom the composition is not administered.

In another aspect, this disclosure describes a method of treating a condition caused by oxidative stress in a subject at risk of having a condition caused by oxidative stress. Generally, the method includes administering to the subject an effective amount of a composition that includes exosomes and/or PEP having at least one antioxidant protein. In some cases, an effective amount of the composition is an amount effective to reduce the likelihood that the subject experiences a symptom or clinical sign of the condition caused by oxidative stress compared to a subject to whom the composition is not administered. In other cases, an effective amount of the composition is an amount effective to reduce the severity of a symptom or clinical sign of the condition caused by oxidative stress compared to a subject to whom the composition is not administered.

In another aspect, this disclosure describes a method of treating tissue damage caused by oxidative stress in a subject. Generally, the method includes administering to the subject a composition that includes exosomes and/or PEP having at least one antioxidant protein in an amount effective to reduce the severity of tissue damage compared to a subject to whom the composition is not administered.

In another aspect, this disclosure describes a method of treating a condition caused by oxidative stress in a subject. Generally, the method includes administering to the subject a composition that includes exosomes and/or PEP having at least one antioxidant protein in an amount effective to reduce the severity of a symptom or clinical sign of the condition caused by oxidative stress compared to a subject to whom the composition is not administered.

In some embodiments of any aspect summarized above, the exosomes and/or PEP are provided in an amount effective to decrease apoptosis in cells of tissue that is oxidatively stressed.

In another aspect, this disclosure describes a method of treating a subject at risk of having a viral infection. Generally, the method includes administering to the subject a composition that includes an effective amount of exosomes and/or PEP having at least one antiviral protein. In some cases, an effective amount is an amount effective to reduce the likelihood that the subject experiences a symptom or clinical sign of the viral infection compared to a subject to whom the composition is not administered. In other cases, an effective amount is an amount effective to reduce the severity of a symptom or clinical sign of the condition caused by the viral infection compared to a subject to whom the composition is not administered. In some embodiments, the antiviral protein can include IFITM-1, IFITM-3, MX1, or viperin.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
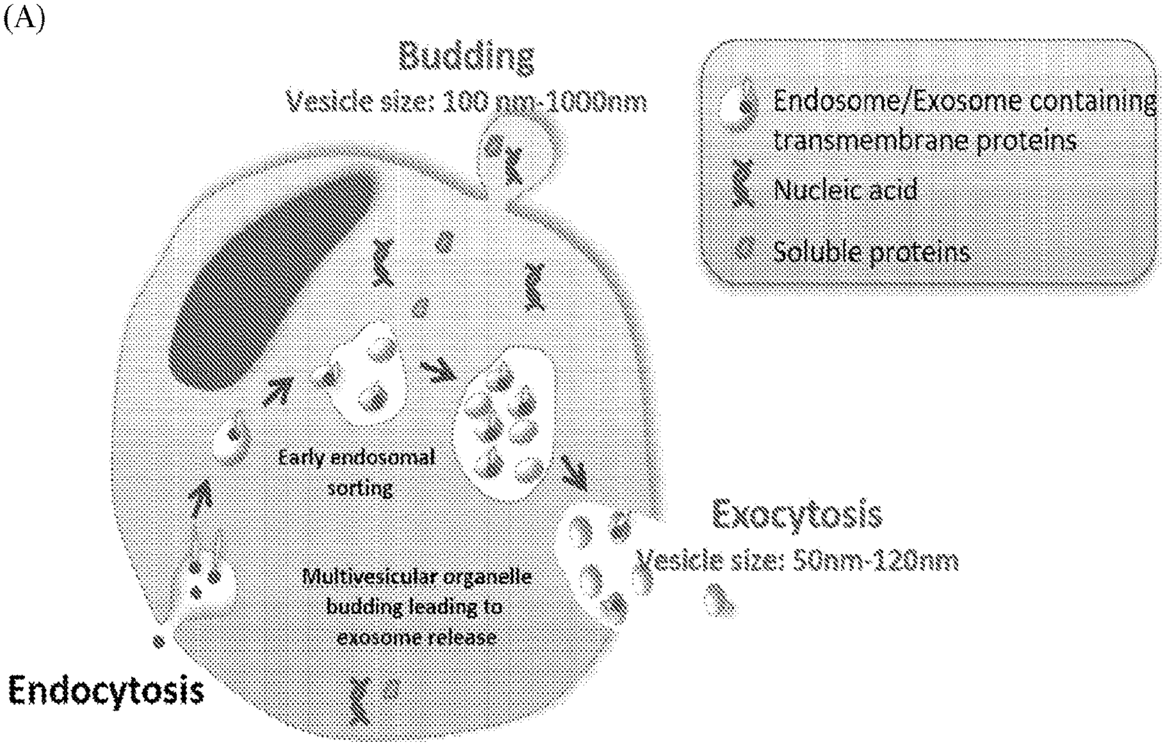
FIG. 1. Schematic of mechanisms of exosome formation and free radical generation. (A) Schematic illustration of exosome production and secretion by cells. (B) Schematic of free radical generation and the antioxidants that inhibit this free radical chain reaction. The compound LY83583 is a superoxide generator when given to cells in culture and was used in several studies to demonstrate that PEP can inhibit the toxic effects of oxidative stress.
Figure 1:
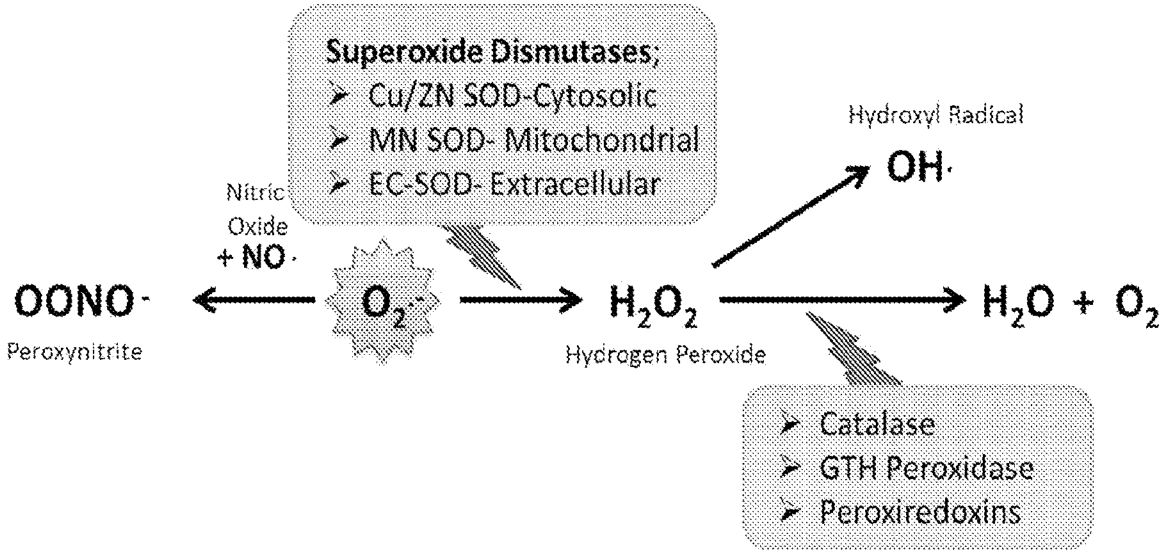

Exosomes are microvesicles (40 nm-100 nm in diameter), secreted from all different cell types and provide cell-to-cell communication signals. A variety of different cargo molecules including miRNA and proteins can be transported between cells via exosomes. Current knowledge of exosomal function in wound healing remains limited.

FIG. 1A is a schematic diagram showing the production of exosomes by a cell. PEP (Purified Exosome Product) is a modified exosome product having unique physical structure compared to standard exosomes. The preparation of PEP from, for example, human blood cells is described in detail in International Patent Application No. PCT/US2018/065627 (International Publication No. WO 2019/118817 A1) and U.S. Patent Application Publication No. US 2021/0169812 A1.

PEP can be formulated into a pharmaceutical composition for many applications. PEP can, for example, augment growth of mesenchymal stems cells (MSCs) and/or dermal fibroblasts to a degree greater than conventional treatments (e.g., platelet lysate) or fetal bovine serum. Similarly, PEP can induce bone differentiation, cartilage differentiation, and/or fat differentiation to a degree greater than conventional treatments (e.g., platelet lysate) or fetal bovine serum. PEP also can maintain growth of myoblasts to a degree greater than conventional treatments (e.g., platelet lysate) or fetal bovine serum. PEP may be employed to enhance growth profiles in cells used for immunotherapies such as, but not limited to, CAR-T, TRUC-T, NK-CAR, and hematopoietic stem cells. (International Patent Application No. PCT/US2018/065627; International Publication No. WO 2019/118817 A1) and U.S. Patent Application Publication No. US 2021/0169812 A1.

PEP compositions and formulation can induce a broad array of cellular responses that are primarily focused around proliferation, anti-apoptosis, immune regulation, and new blood vessel formation. Injured tissues in the presence of PEP have a propensity towards regeneration. This response is embodied with observations that document augmented expression of transforming growth factor beta (TGF-β), vascular endothelial growth factor (VEGF), epidermal growth factor (EFG), fibroblast growth factor (FGF), hepatocyte growth factor (HGF), and platelet-derived growth factor (PDGF). The response is not limited to these factors but the observation that these factors are induced in different tissues is an embodiment of the regenerative influence of PEP.

This disclosure describes antioxidant and antiviral properties of exosomes, both native exosomes and PEP, that lead to additional therapeutic and/or prophylactic applications. While described herein in the context of an exemplary embodiment of PEP and/or exosomes, the compositions and methods described herein can involve any extracellular vesicle that includes the protein or proteins responsible for conferring antioxidant or antiviral properties to PEP and/or exosomes. For example, the compositions and methods described herein can involve extracellular vesicles regardless of their mechanism of origin and release from a cell. While exosomes are generally 50 nm to 150 nm in size and have a specific biological mechanism of origin, extracellular vesicles have multiple biological mechanisms of origin and can range from 50 nm to 1000 nm in size.

Antioxidant Activity

For example, cardiovascular disease is a leading cause of mortality and morbidity worldwide. A toxic environment exists in disease conditions whereby elevated levels of free radicals cause oxidative stress and increased immune cell activity. This increase in immune cell activity can contribute to the development of cardiovascular disease. Antioxidants combat the effects of free radicals by catalyzing the transformation of free radicals to stable, non-radical compounds (FIG. 1). Exosomes and PEP contain antioxidants and evade immune response, making each of them useful in alleviating a toxic disease environment.

Figure 7:
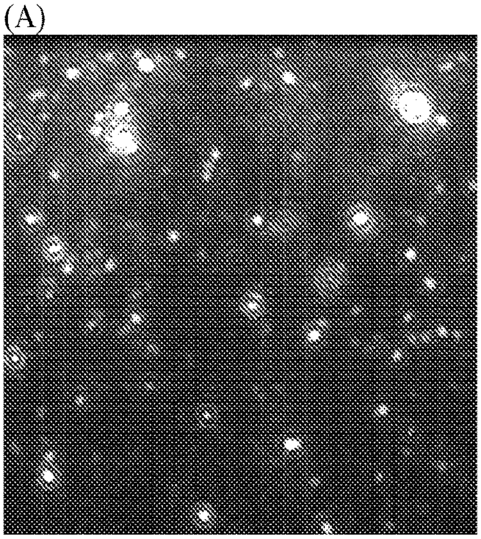
FIG. 7. Characterization of exosomes in PEP. (A) NANOSIGHT (Malvern Panalytical Ltd., Salisbury, UK) image of exosomes in PEP. (B) NANOSIGHT quantification of size and number of exosomes in 20% PEP (18001-B2). (C) Western Blot analysis of known markers of exosomes in three separate preparations of PEP.
Figure 7:
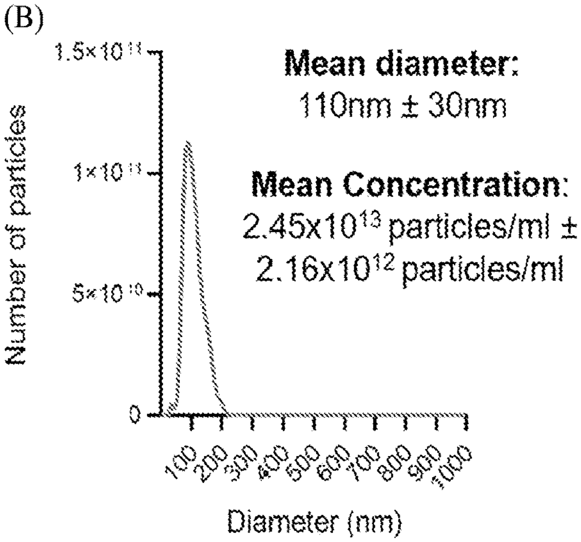
Figure 7:
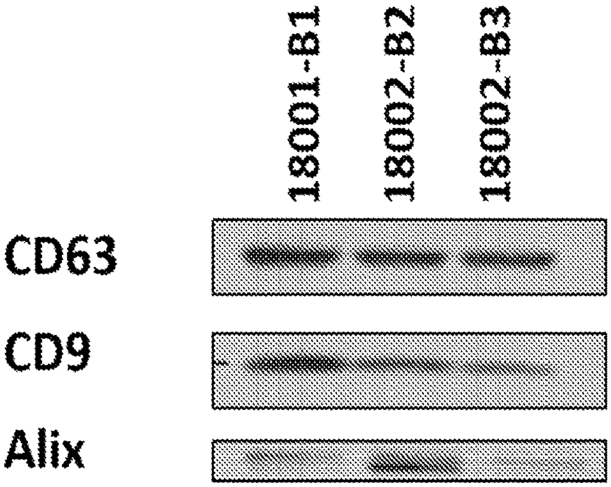

FIG. 7A is a representative NANOSIGHT (Malvern Panalyical Ltd., Salisbury, UK) image of PEP particles. FIG. 7B shows NANOSIGHT quantification of size and number of PEP particles in 20% reconstituted PEP preparation (PEP diluted in serum free media to 20% of the stock concentration). FIG. 7C shows Western blot analysis of known markers exosomes in three separate preparations of PEP.

Figure 2:
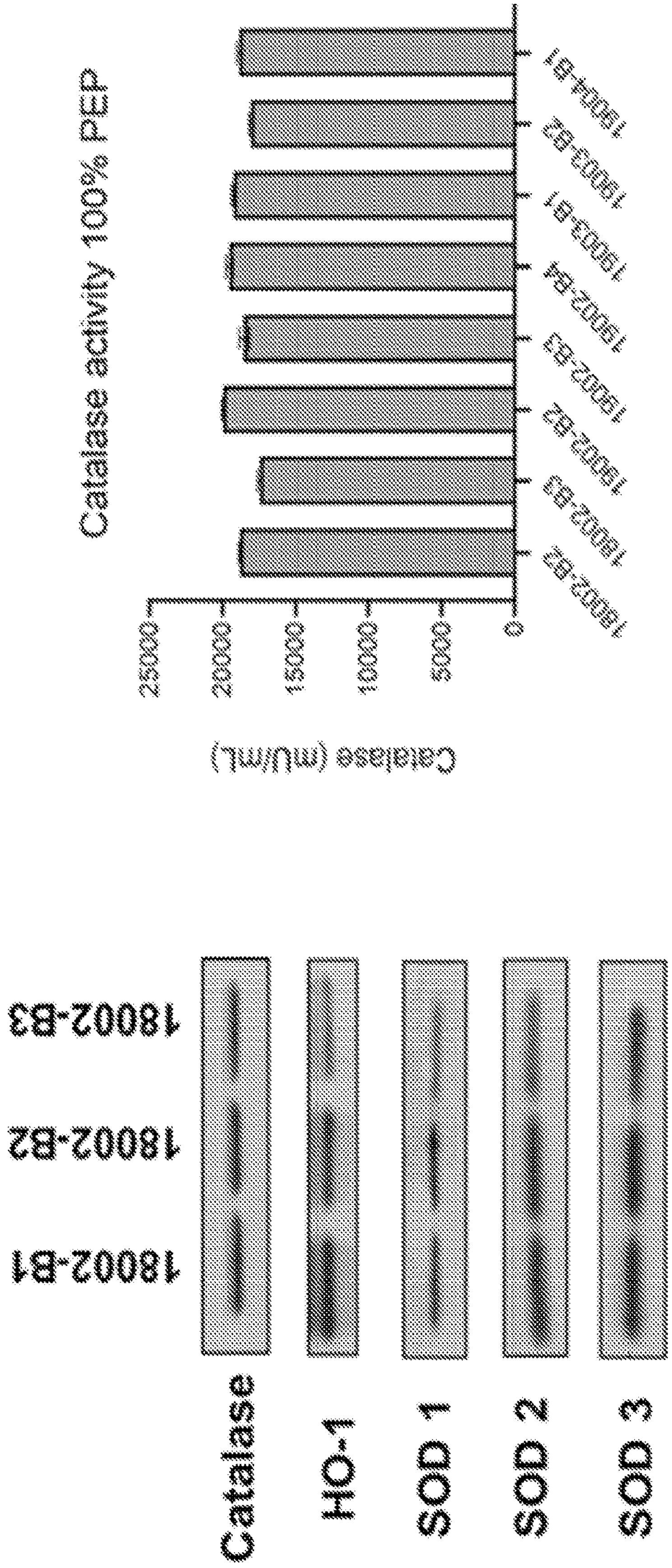
FIG. 2. Antioxidant expression in three different PEP preparations. (A) Western blot analysis of antioxidant proteins in PEP samples. Heme oxygenase-1 (HO-1), Cu/Zn Superoxide dismutase (SOD 1), Mn superoxide dismutase (SOD 2), Extracellular superoxide dismutase (SOD 3). (B) Quantification of catalase activity in several preparations of PEP.

FIG. 2 shows data demonstrating the presence of antioxidant expression in different PEP preparations. Each preparation was prepared the same way, but the starting material from each preparation was from different batch productions of PEP. FIG. 2A shows Western blot analysis of five antioxidant proteins in PEP samples: catalase, heme oxygenase-1 (HO-1), Cu/Zn superoxide dismutase (SOD 1), Mn superoxide dismutase (SOD 2), and extracellular superoxide dismutase (SOD 3). FIG. 2B shows quantification of catalase and superoxide dismutase (SOD) expression in each of eight different PEP preparations.

Figure 3:
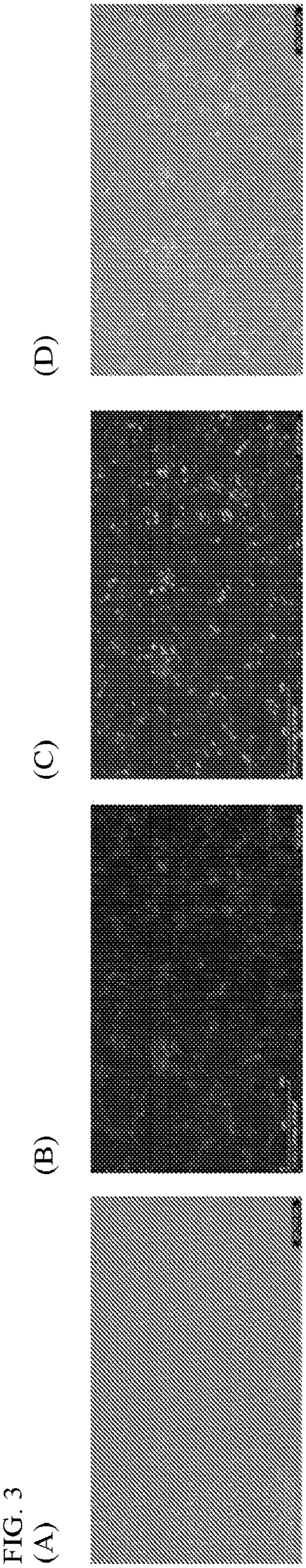
FIG. 3. PEP reduces oxidative stress in primary neural cells. Murine neurons in vitro were treated with or without PEP prior to treatment with the superoxide generator LY83583 (1 M) for 24 hours. Cell death was detected using a caspase 3/7 specific dye that causes apoptotic cells to turn red. (A) Phase microscopy of murine neurons. (B) Fluorescent microscopy image of (A). Red caspase 3/7 dye is visible in cells treated with LY83583 alone. (C) Neurons were also labeled with NucLight green to detect nuclei of cells. (D) Merged images of B-D. (E) Quantification of caspase 3/7 positive cells using an INCUCYTE S3 cell imager (Essen Bioscience, Inc., Ann Arbor, MI). In The absence of PEP, LY83583 induces apoptosis of neurons after 24 hours of LY83583 treatment. In contrast, PEP pretreatment for one hour inhibits oxidative stress.
Figure 3:
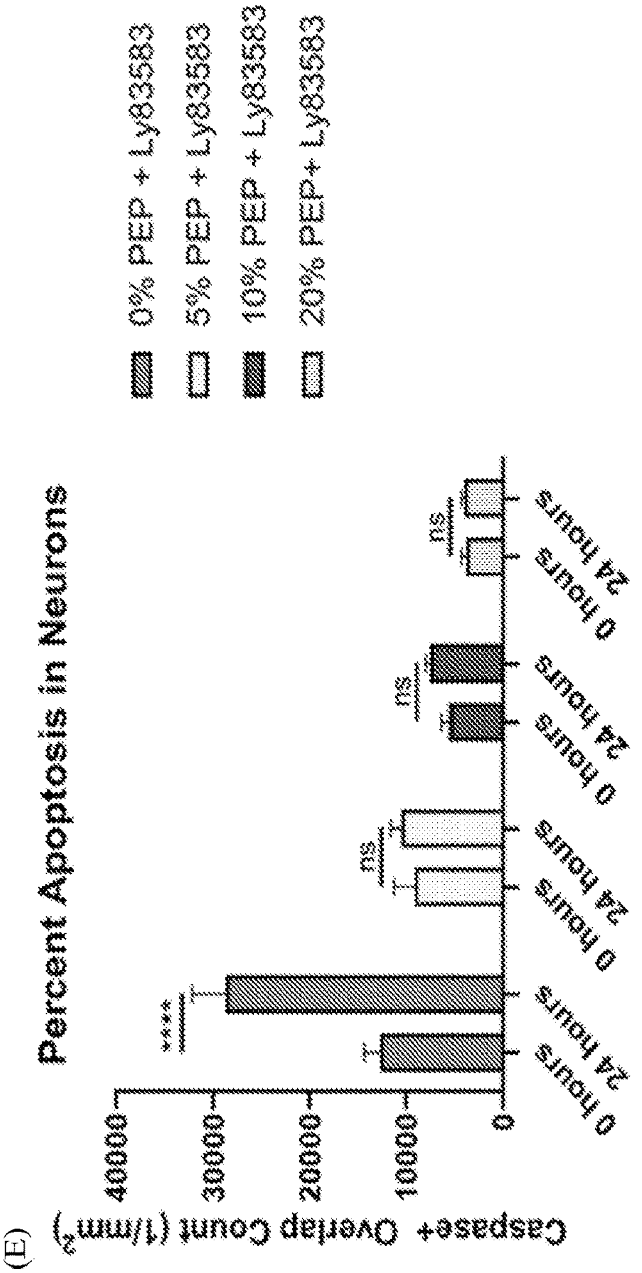
Figure 4:
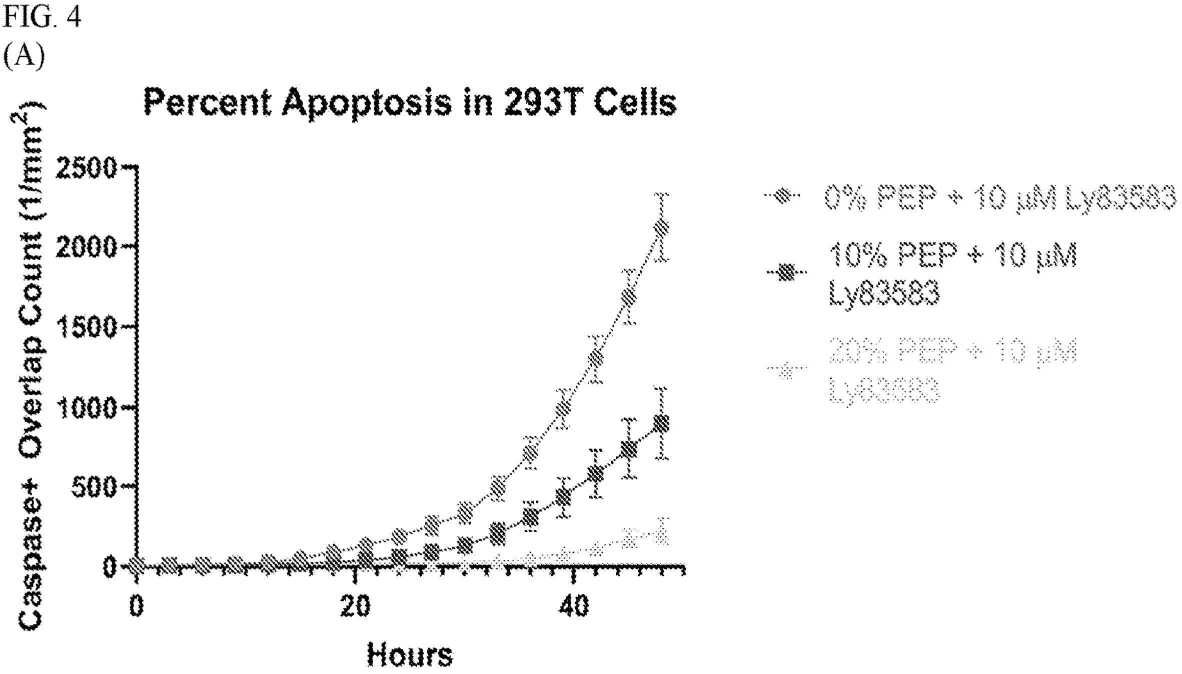
FIG. 4. Dose-dependent effects of PEP on oxidative stress in human embryonic kidney 239T cells (HEK239T or 293T) cells. (A) Pretreatment of 293T cells with PEP inhibits LY83583-induced oxidative stress in a dose-dependently manner. Murine neurons were treated in vitro with or without PEP prior to treatment with the superoxide generator LY83583 (1 μM) for 24 hours. (B) Confocal microscopy image showing apoptotic cells following treatment with LY83583 alone. (C) Confocal microscopy image showing apoptotic cells following treatment with LY83583 and 10% PEP. (D) Confocal microscopy image showing apoptotic cells following treatment with LY83583 and 20% PEP. Cell death was detected using a caspase 3/7 specific dye that causes dying cells to turn red. Analysis was quantified using an INCUCYTE S3 cell imager (Essen Bioscience, Inc., Ann Arbor, MI).
Figure 4:
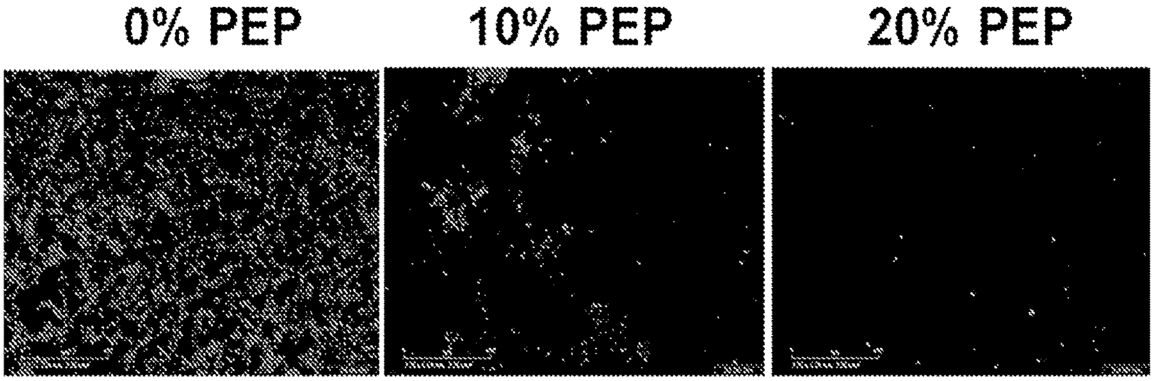
Figure 5:
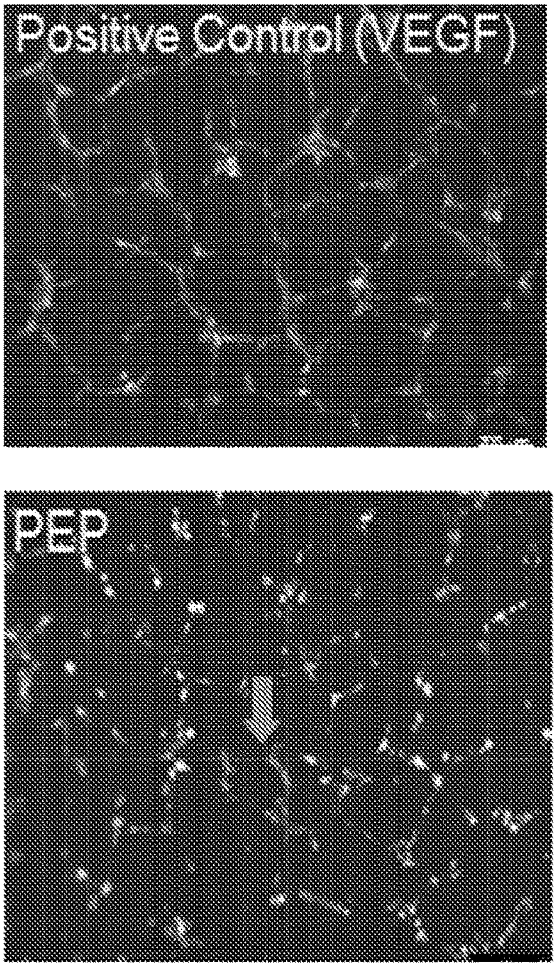
FIG. 5. PEP inhibits oxidative stress in primary human umbilical endothelial cells (HUVEC). HUVEC cells in vitro were treated with or without PEP prior to treatment with the superoxide generator LY83583 (20 μM) for five hours. Live cell imaging was performed to watch tube formation over time using an INCUCYTE S3 cell imager (Essen Bioscience, Inc., Ann Arbor, MI). Representative fluorescent images of endothelial tube formation.
Figure 6:
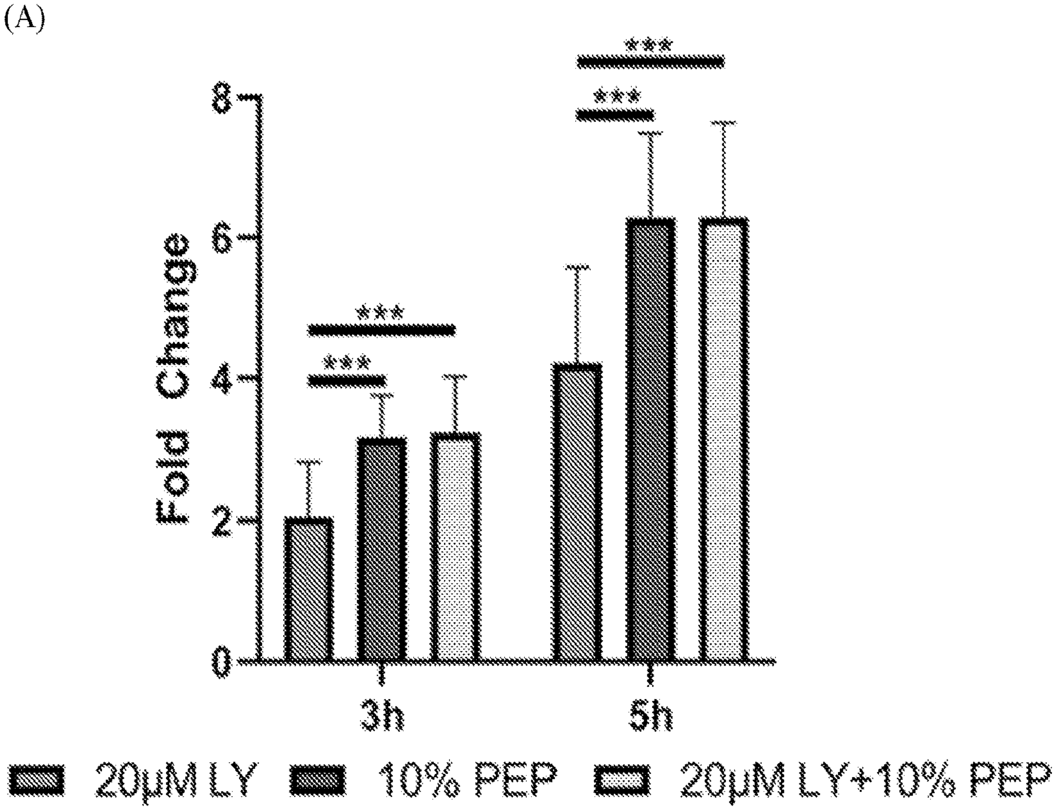
FIG. 6. PEP inhibits oxidative stress in primary human umbilical endothelial cells (HUVEC). HUVEC cells in vitro were treated with or without PEP prior to treatment with the superoxide generator LY83583 (20 μM) for five hours. (A) Quantification of vessel percentage area. (B) Quantification of vessel length. Tube formation was measured using ImageJ software. PEP pretreatment significantly enhanced tube formation in a setting of oxidative stress as determined by total vessel percentage and vessel length.
Figure 6:
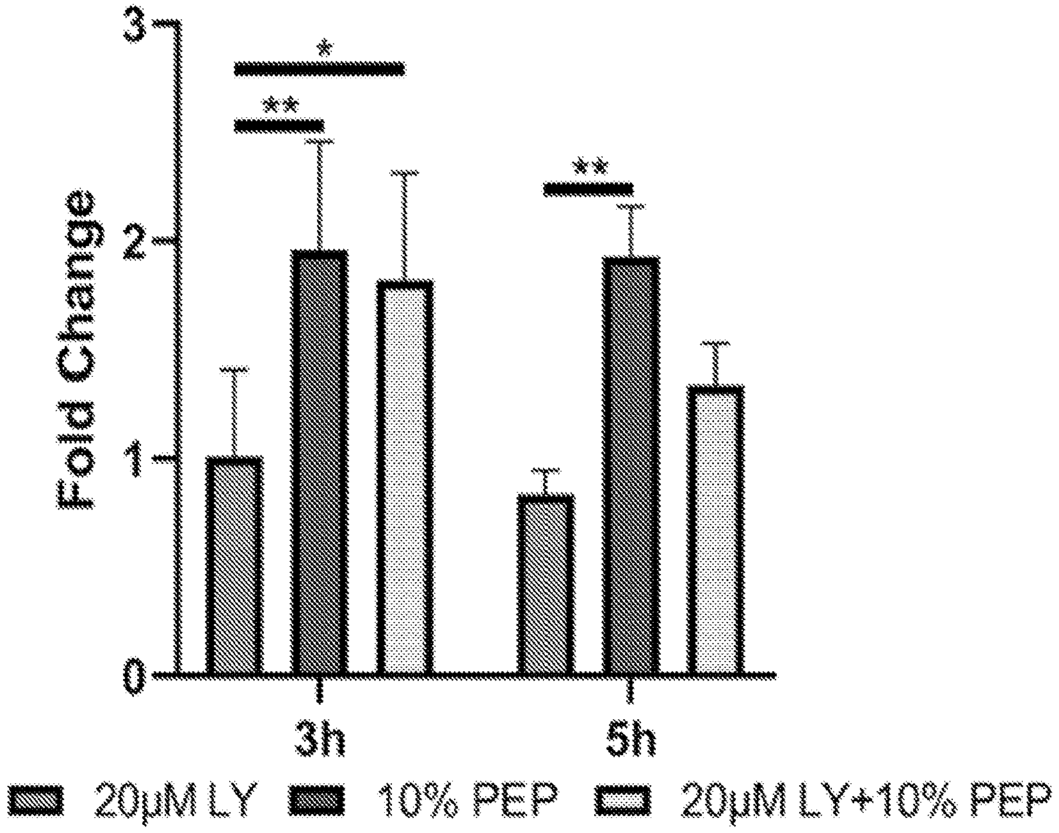

FIG. 3 shows dose-dependent effects of PEP on oxidative stress in 293T cells. Cells pre-treated with PEP are less apoptotic after LY83583-induced oxidative stress (FIG. 3A-D). Moreover, the effect of PEP pre-treatment is dose dependent. Confocal microscopy images confirming the dose-dependent decrease in apoptosis as the neural cells are pre-treated with increasing concentration of PEP. FIGS. 4-6 provide data demonstrating the antioxidant effects of PEP in other 293T cells (FIG. 4) and human umbilical endothelial cells (HUVEC; FIG. 5 and FIG. 6).

In some embodiments, the antioxidants may be inducible antioxidants within exosomes or the exosomes from which PEP is prepared. While exosomes and/or PEP can contain endogenous antioxidants, antioxidants in exosomes and/or PEP can upregulated by preconditioning the source of exosomes to stress. These stress inducers may include, but are not limited to, hypoxia, hyperthermia, chemical-induced, or radiation.

Exosomes and/or PEP can therefore be used to inhibit oxidative stress in diseased tissues. Pre-treating cells with exosomes and/or PEP that contains antioxidants reduces the effects of oxidative stress associated with many diseases.

Thus, this disclosure describes methods for treating a subject having, or at risk of having, a disease caused, at least in part, by oxidative stress. As used herein, the term "at risk" refers to a subject that may or may not actually possess the described risk. Thus, for example, a subject "at risk" of a condition caused, at least in part by oxidative stress, is a subject possessing one or more risk factors associated with the condition such as, for example, genetic predisposition, ancestry, age, sex, geographical location, lifestyle, or medical history.

Accordingly, a composition that includes exosomes and/or PEP can be administered before, during, or after the subject first exhibits a symptom or clinical sign of a condition caused, at least in part by oxidative stress. Treatment initiated before the subject first exhibits a symptom or clinical sign associated with the condition is considered prophylactic treatment and may result in decreasing the likelihood that the subject experiences clinical evidence of the condition compared to a subject to which the composition is not administered, decreasing the severity of symptoms and/or clinical signs of the condition, and/or completely resolving the condition. Treatment initiated after the subject first exhibits a symptom or clinical sign associated with the condition is considered to be therapeutic and may result in decreasing the severity of symptoms and/or clinical signs of the condition compared to a subject to which the composition is not administered, and/or completely resolving the condition.

Thus, the method includes administering an effective amount of a composition that include exosomes and/or PEP to a subject having, or at risk of having, a particular disease condition. In this aspect, an "effective amount" is an amount effective to reduce, limit progression, ameliorate, or resolve, to any extent, a symptom or clinical sign related to the condition.

Antiviral Activity

The interferon (IFN) system is the first line of defense in humans against animal viruses. Binding of type I IFNs or type III IFNs to their receptors (IFNAR1/2 and IL-28Rα/IL-10Rβ, respectively) induces an antiviral state within the cell by inducing the transcription of IFN-stimulated genes, including interferon inducible transmembrane proteins (IFITM-1, IFITM-3, and IFITM-5), viperin, RNA-activated protein kinase (PKR), ribonuclease L (RNase L), myxoma resistance protein 1 (MX1) and oligoadenylate synthases (OASs).

Figure 8:
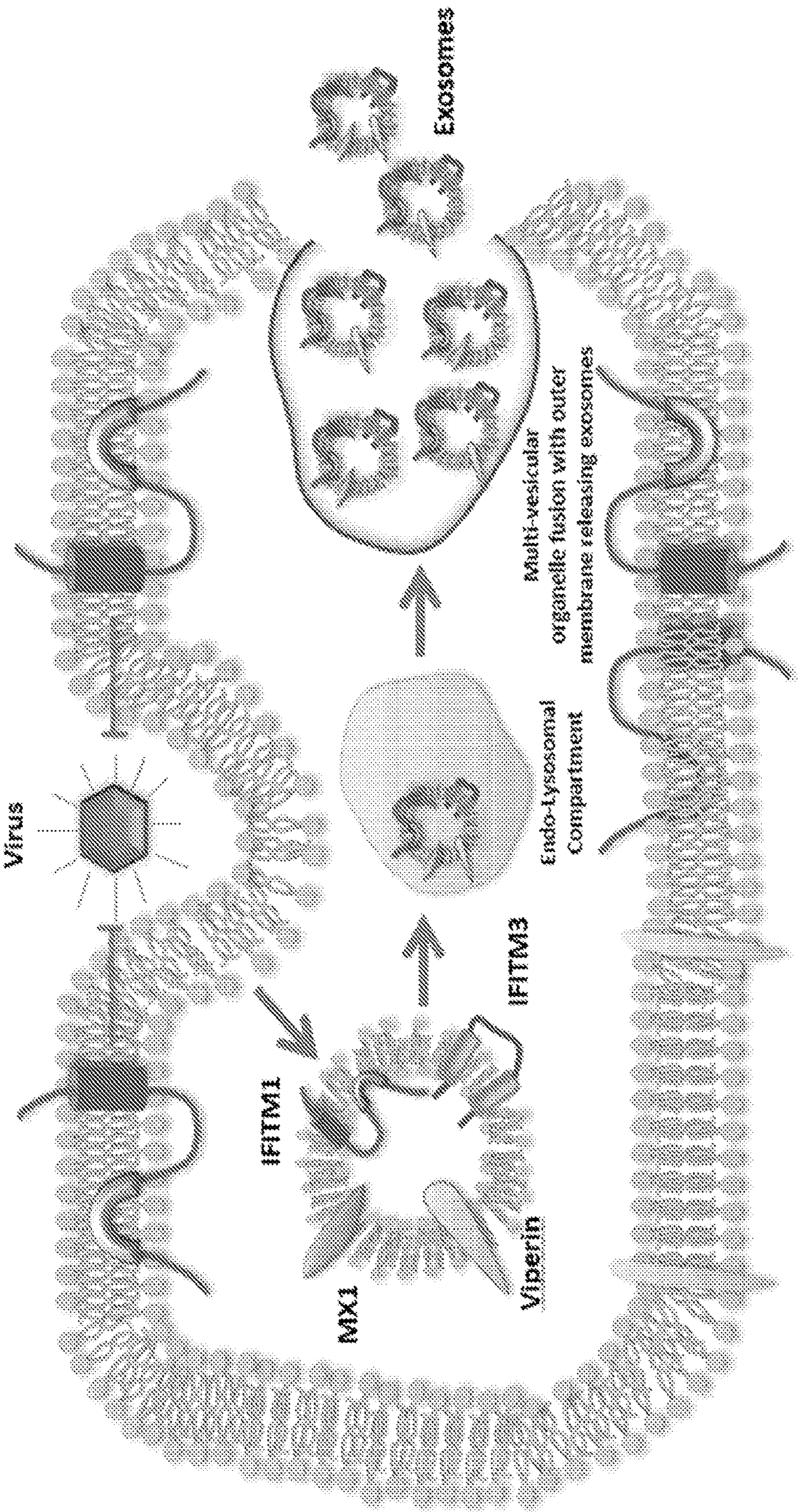
FIG. 8. Schematic illustration depicting antiviral proteins including Interferon Inducible transmembrane proteins 1,3 (IFITM) as well as MX1 and viperin being packaged into exosomes. These antiviral proteins are contained within exosomes and also in preparations of PEP.
Figure 9:
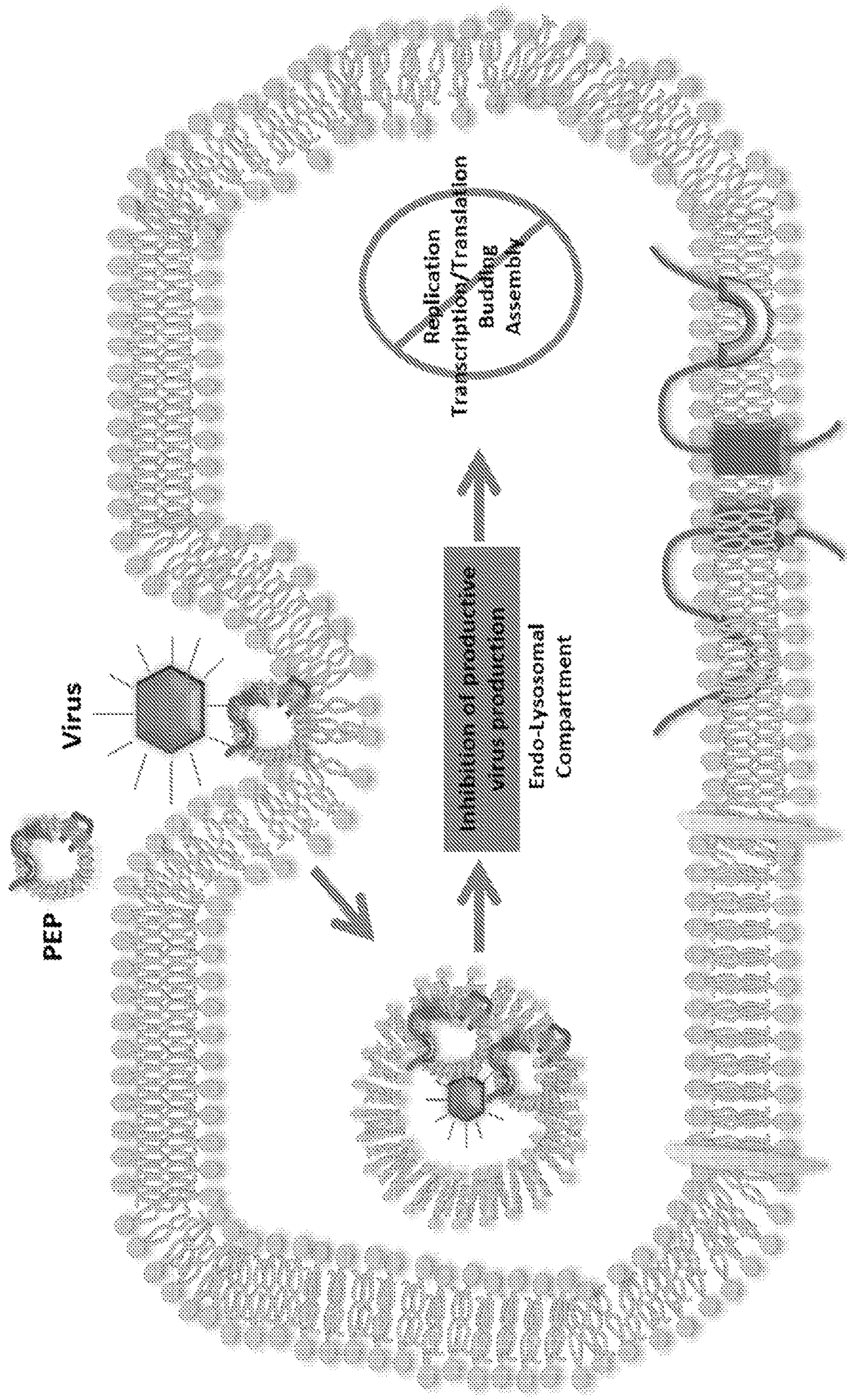
FIG. 9. Schematic illustration depicting the mechanism through which PEP may inhibit virus production. Pre-treatment and post-treatment with PEP inhibits viral entry into cells. The antiviral proteins in PEP are responsible for this inhibition.
Figure 10:
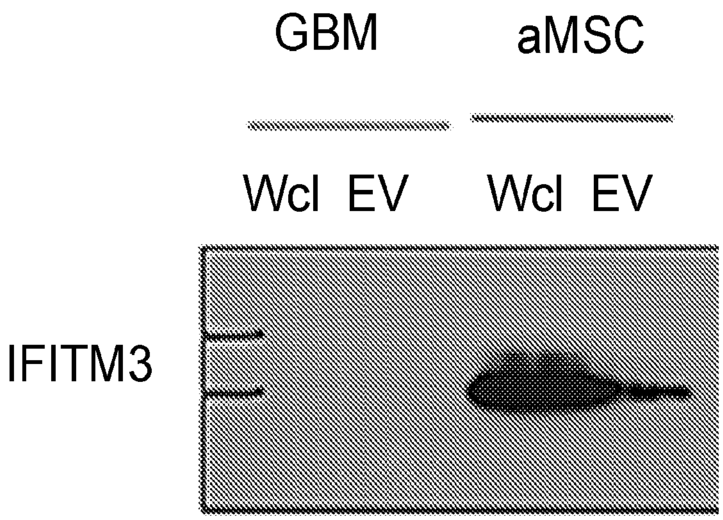
FIG. 10. Characterization of antiviral proteins in glioblastoma (GBM) and adipose-derived mesenchymal stem cell (aMSC) cell lines. (A) IFITM3 was found in both the whole cell lysate (WCL) and PEP prepared from aMSC, but not GBM. (B) IFITM1 was found to be expressed in three different preparations of PEP.
Figure 10:
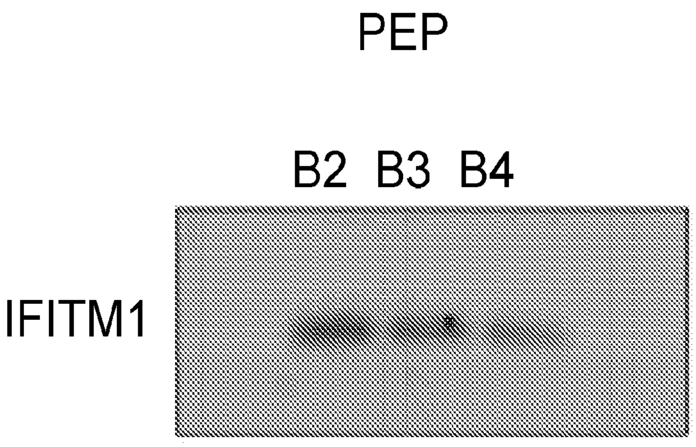

FIG. 8 is a schematic illustration depicting antiviral proteins such as Interferon Inducible transmembrane proteins 1,3 (IFITM), MX1, and viperin being packaged into exosomes. These antiviral proteins are also present in PEP. FIG. 9 is a schematic illustration depicting a possible mechanism through which PEP and/or exosomes may inhibit virus production. Pre-treatment and post-treatment with PEP inhibits viral entry into cells. The antiviral proteins in PEP and/or exosomes are responsible for this inhibition.

Interferon-induced transmembrane proteins IFITMs are members of the IFITM family (Interferon-induced transmembrane protein), which are encoded by IFITM genes. The human IFITM genes locate on chromosome 11 and have four members: IFITM1, IFITM2, IFITM3, and IFITM5. IFITM proteins have been identified as antiviral restriction factors for influenza A virus replication. Knockout of IFITM3 increases influenza virus A replication and overexpression of IFITM3 inhibits influenza virus A replication. IFITM proteins also are able to inhibit infection by several other enveloped viruses belonging to different virus families. These viruses include flaviviruses (dengue virus and West Nile virus), filoviruses (Marburg virus and Ebola virus) coronaviruses (SARS coronavirus) and lentivirus (Human immunodeficiency virus). IFITM3 knockout increases Swine flu virus multiplication, while overexpression reduces viral levels.

Interferon-induced GTP-binding protein Mx1 is a protein that in humans is encoded by the MX1 gene. In mouse, the interferon-inducible Mx protein is responsible for a specific antiviral state against influenza virus infection. The human protein is similar to the mouse protein as determined by its antigenic relatedness, induction conditions, physicochemical properties, and amino acid analysis. This cytoplasmic protein is a member of both the dynamin family and the family of large GTPases.

Viperin (Virus inhibitory protein, endoplasmic reticulum-associated, interferon-inducible), also known as RSAD2 (radical SAM domain-containing 2), is a multifunctional protein in viral processes. Viperin is a cellular protein that can inhibit many DNA and RNA viruses such as, for example, CHIKV, HCMV, HCV, DENV, WNV, SINV, influenza, and HIV-1 LAI strain.

In some cases, exosomes or PEP can be transformed into antiviral particles capable of inhibiting viral entry and replication. Exosomes can contain endogenous antiviral proteins that remain present throughout the preparation of PEP. Exosomes and/or PEP can be further modified to include a polynucleotide that encodes an miRNA that also interferes with viral replication. Suitable such miRNAs include, but are not limited to, miR-127-3p, miR-486-5p, miR-593-5p, miR-196, miR-199a-3p, miR-296, miR-351, miR-431 and miR-448.

Figure 11:
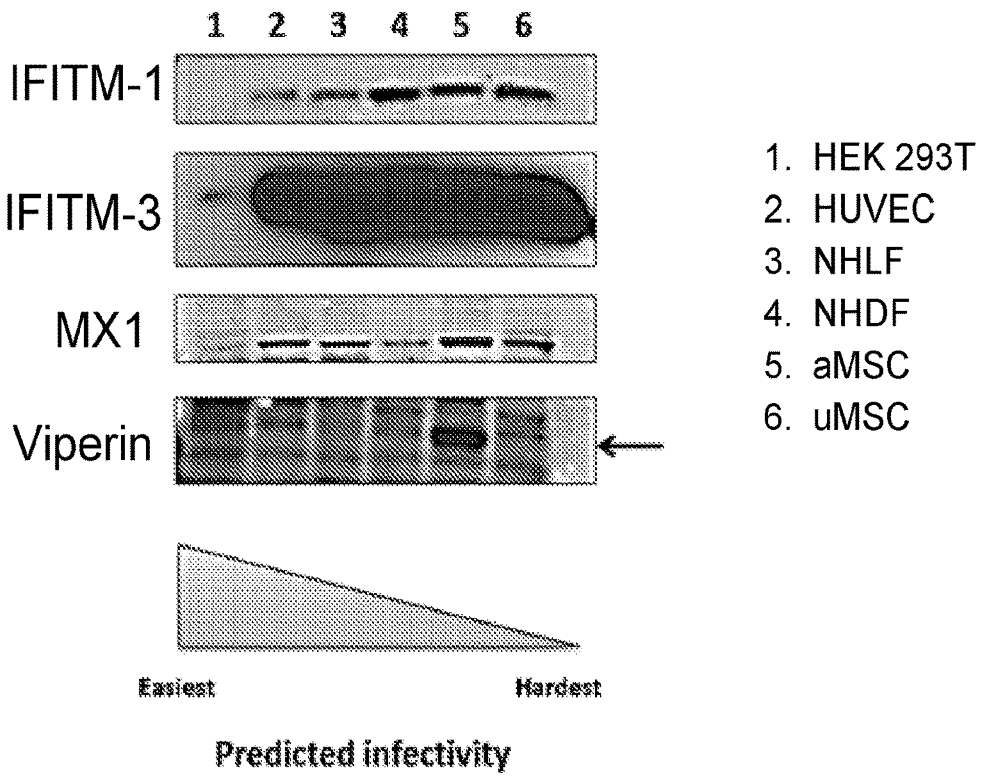
FIG. 11. Characterization of antiviral proteins in six different cell lines. Western blot of cell lysates probing for IFITM-1, IFITM-3, MX1, and viperin. Lane 1: Human embryonic kidney cells (HEK 293T); Lane 2: Human umbilical vein endothelial cells (HUVECs); Lane 3: Normal human lung fibroblasts (NHLF); Lane 4: Normal human dermal fibroblasts (NHDF); Lane 5: adipose-derived mesenchymal stem cells (aMSC); Lane 6: Umbilical cord-derived mesenchymal stem cells (uMSC). Predicted infectivity is derived from amount of antiviral proteins depicted by the Western blot—i.e. Lane 1 (HEK293T) has the least amount of IFITM protein and would therefore is predicted to be the easiest to infect.
Figure 12:
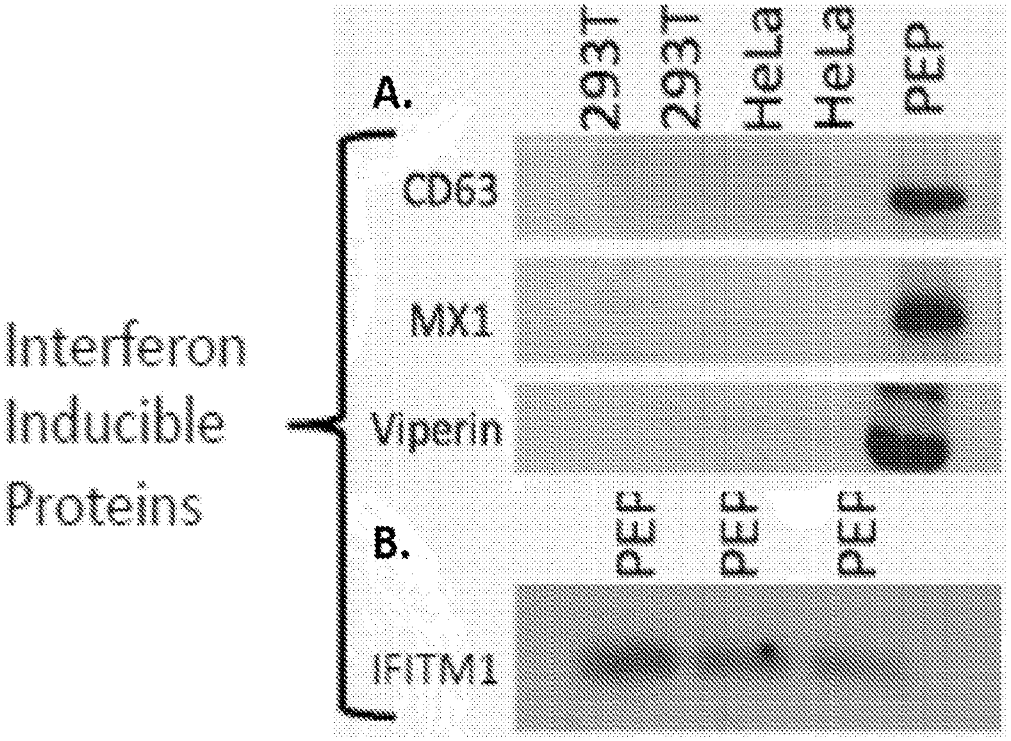
FIG. 12. Characterization of protein expression in PEP. (A) Western blot comparing protein expression levels of the exosome marker CD63 and antiviral proteins MX1 and viperin in 293T cells, Hela cells, and PEP. (B) Comparison of IFITM1 expression in three different production batches of PEP.

FIG. 11 shows characterization of antiviral proteins in six different cell lines. The cell lines tested were Human embryonic kidney cells (HEK 293T), Human umbilical vein endothelial cells (HUVECs), Normal human lung fibroblasts (NHLF), Normal human dermal fibroblasts (NHDF), adipose-derived mesenchymal stem cells (aMSC), Umbilical cord-derived mesenchymal stem cells (uMSC). Inhibiting viral replication in humans may be particularly useful as antiviral prophylactic (pre-infection) or therapeutic (post-infection) treatments. Different cell types contain different antiviral proteins, which can be found in exosomes and/or PEP. Thus, the antiviral cargo of a PEP preparation can be designed, at least in part, by the cell type used as the starting material for preparing the PEP.

Figure 13:
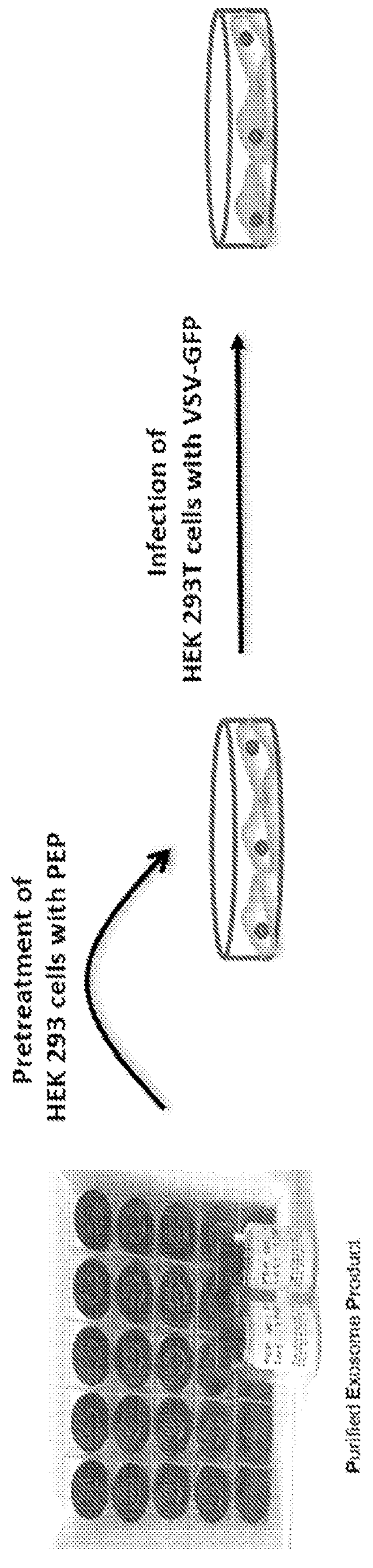
FIG. 13. Schematic illustration summarizing the in vitro experimental design. (A) Pre-treatment of 293T cells with PEP. (B) Treatment of 293T cells with PEP after viral infection.
Figure 13:
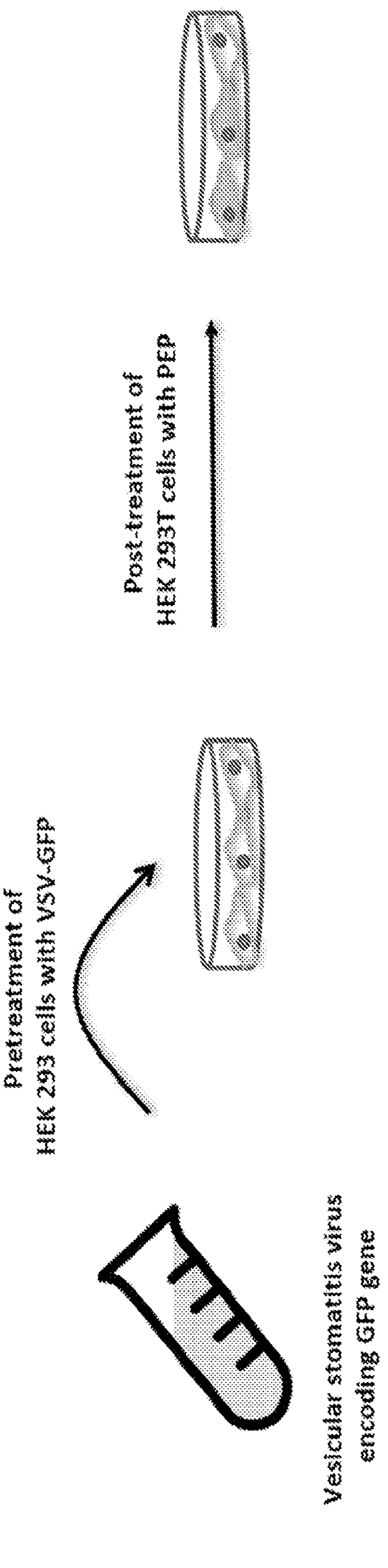
Figure 14:
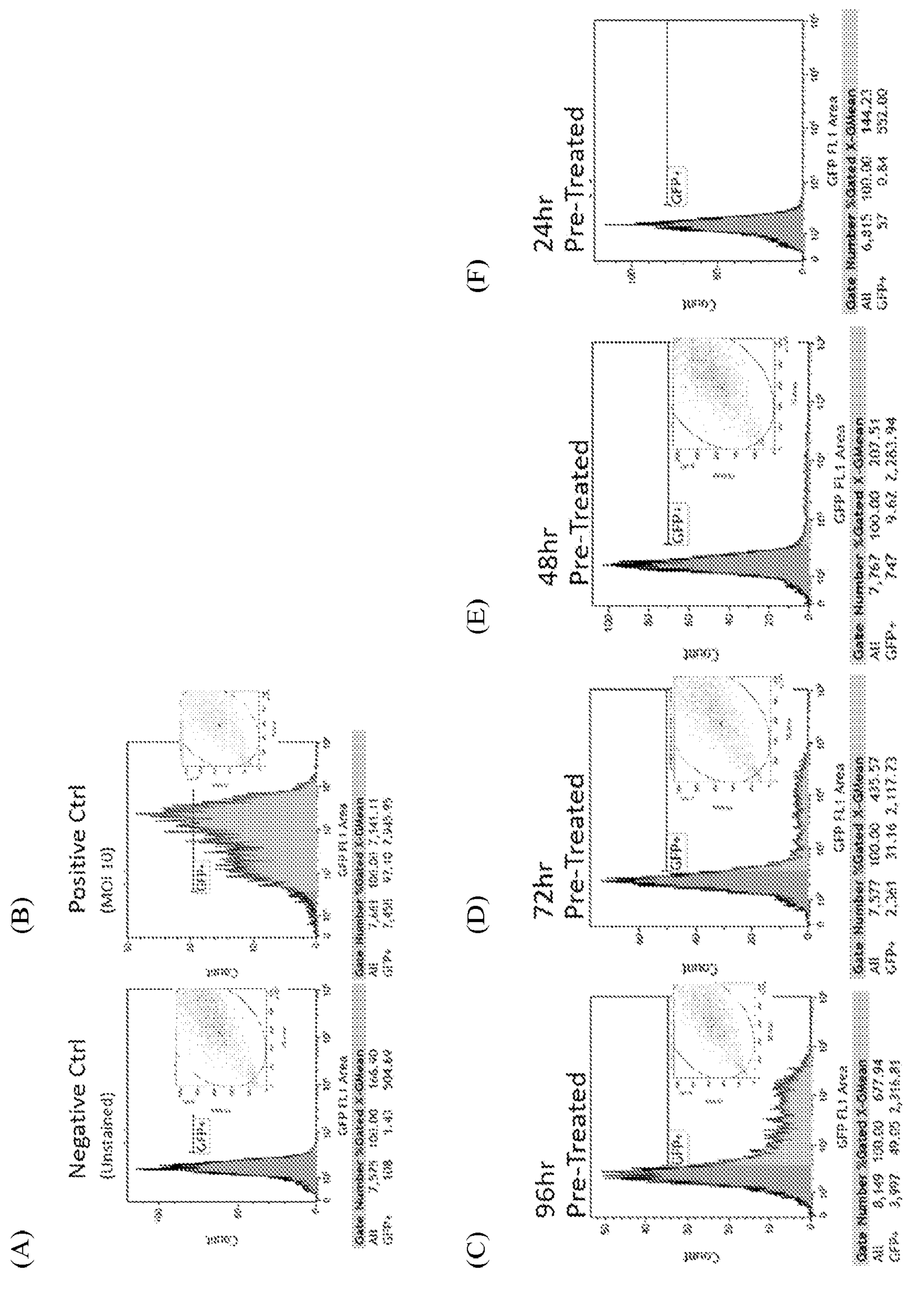
FIG. 14. Pre-treating cells with PEP inhibits viral infection. 293T cells were seeded in a six-well plate at 300,000 cells/well. Cells were pre-treated with PEP for 96 hours, 72 hours, 48 hours, or 24 hours before VSV-GFP infection at a multiplicity of infection (MOI) of 10. VSV-GFP ($2.37\times10^5$ PFU/ml) was diluted in serum-free media for an MOI of 10. 24 hours after infection, cells were fixed in 2% PFA and subjected to flow cytometry to determine the number of infected cells that became green after infection. (A) Negative control: unstained cells. (B) Positive control: 293T cells infected with VSV-GFP at an MOI of 10 without PEP pre-treatment. (C) 293T cells treated with PEP for 96 hours prior to viral infection. (D) 293T cells treated with PEP for 72 hours prior to viral infection. (E) 293T cells treated with PEP for 48 hours prior to viral infection. (F) 293T cells treated with PEP for 24 hours prior to viral infection. PEP pre-treatment significantly inhibited viral infection, particularly within 48 hours of exposure.

FIG. 13 shows the experimental design of investigations into the in vitro antiviral activity of PEP. FIG. 13A illustrates the design of experiments to test whether prophylactic pretreatment of cells with PEP can inhibit viral infection. Viral infection was monitored by infecting cells with VSV-GFP, which causes infected cells to express green fluorescent protein (GFP). FIG. 14 shows that cells pre-treated with antiviral PEP prior to VSV-GFP transduction had a significant decrease in number of GFP-positive cells compared to the positive control. Cells treated 24 hours prior to transduction showed little to no GFP positive cells and represented more similarly to that of the negative control.

Figure 15:
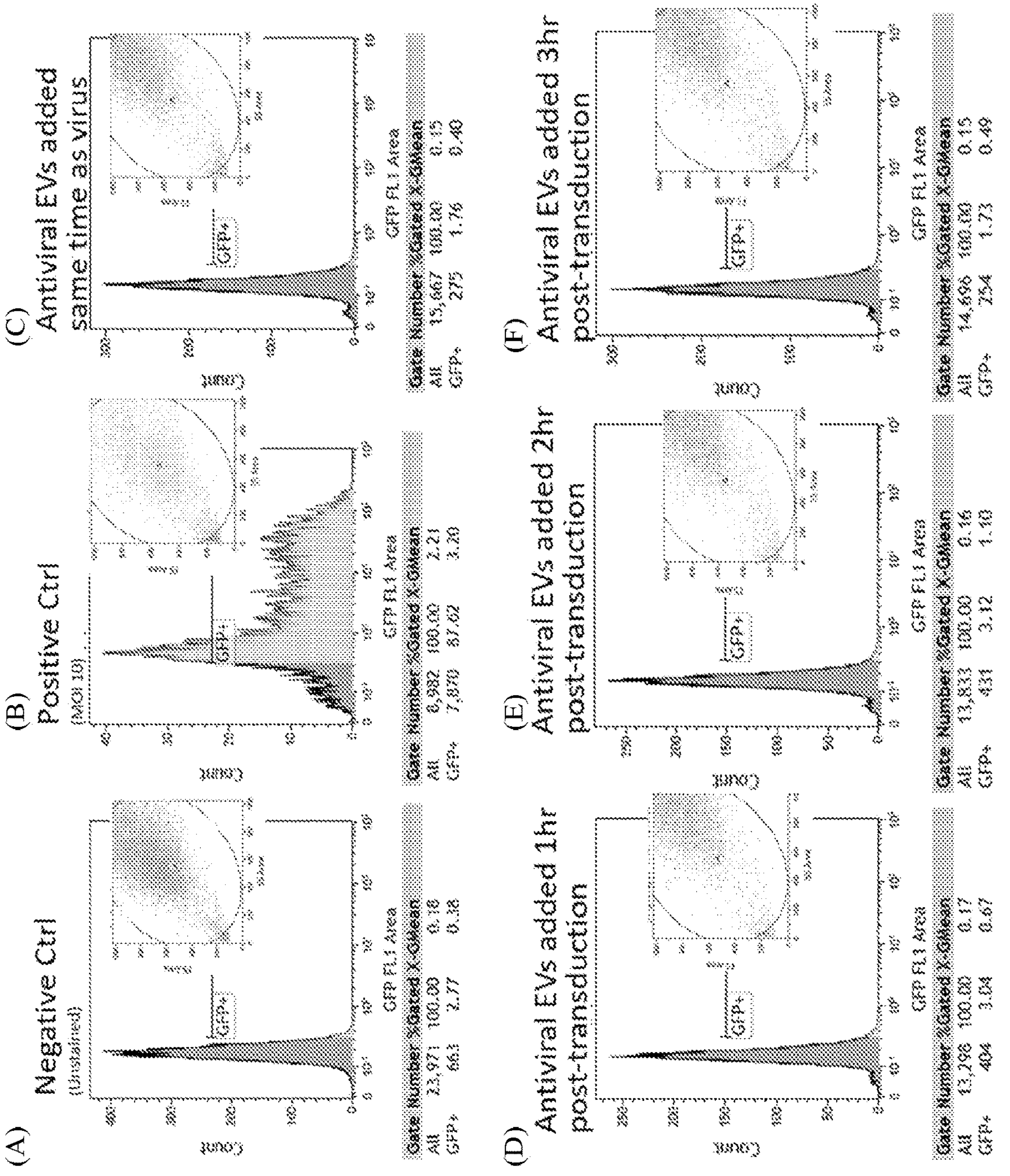
FIG. 15. Treating cells with PEP after viral infection inhibits spread if viral infection. 293T cells were transduced with VSV-GFP (MOI 10), then treated with PEP at the same time as transduction, one hour after transduction, two hours after transduction, or three hours after transduction. PEP post-treatment significantly protects the cells from viral infection. 24 hours after transduction, cells were fixed in 2% PFA and subjected to flow cytometry to determine the number of infected cells that became green after infection. (A) Negative control: unstained cells. (B) Positive control: 293T cells infected with VSV-GFP at an MOI of 10 without PEP pre-treatment. (C) 293T cells treated with PEP at the same time as exposure to virus. (D) 293T cells treated with PEP one hour after exposure to virus. (E) 293T cells treated with PEP two hours after exposure to virus. (F) 293T cells treated with PEP three hours after exposure to virus.
Figure 16:
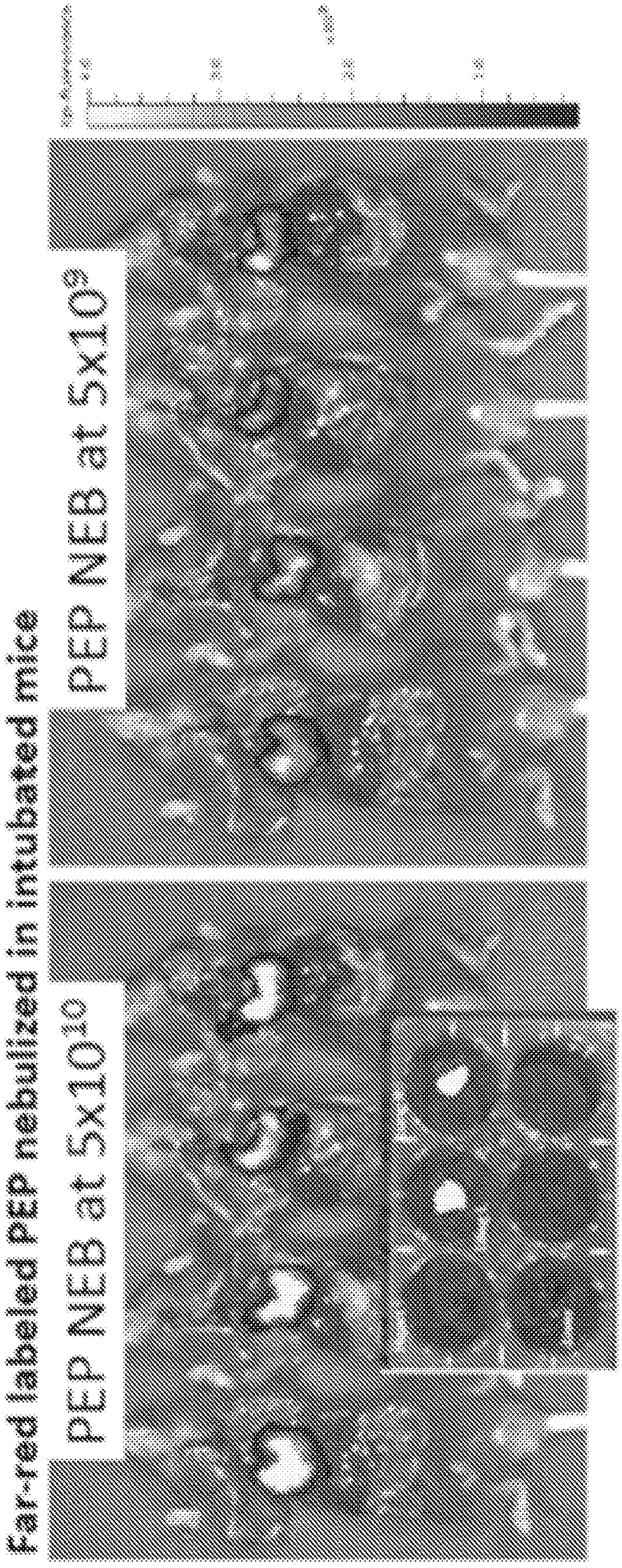
FIG. 16. In vivo uptake of PEP into murine lungs by nebulization. Nebulized PEP penetrates to alveolar bed with epithelial uptake. DiR-labeled PEP in saline was given at different doses over the course of five minutes using a ventilator (FLEXIVENT; SCIREQ Scientific Respiratory Equipment, Inc., Montreal, Quebec, Canada) to deliver the nebulized PEP. Images were obtained using a XENOGEN imager (IVIS 200, Caliper Life Sciences, Inc., Hopkinton, MA).
Figure 17:
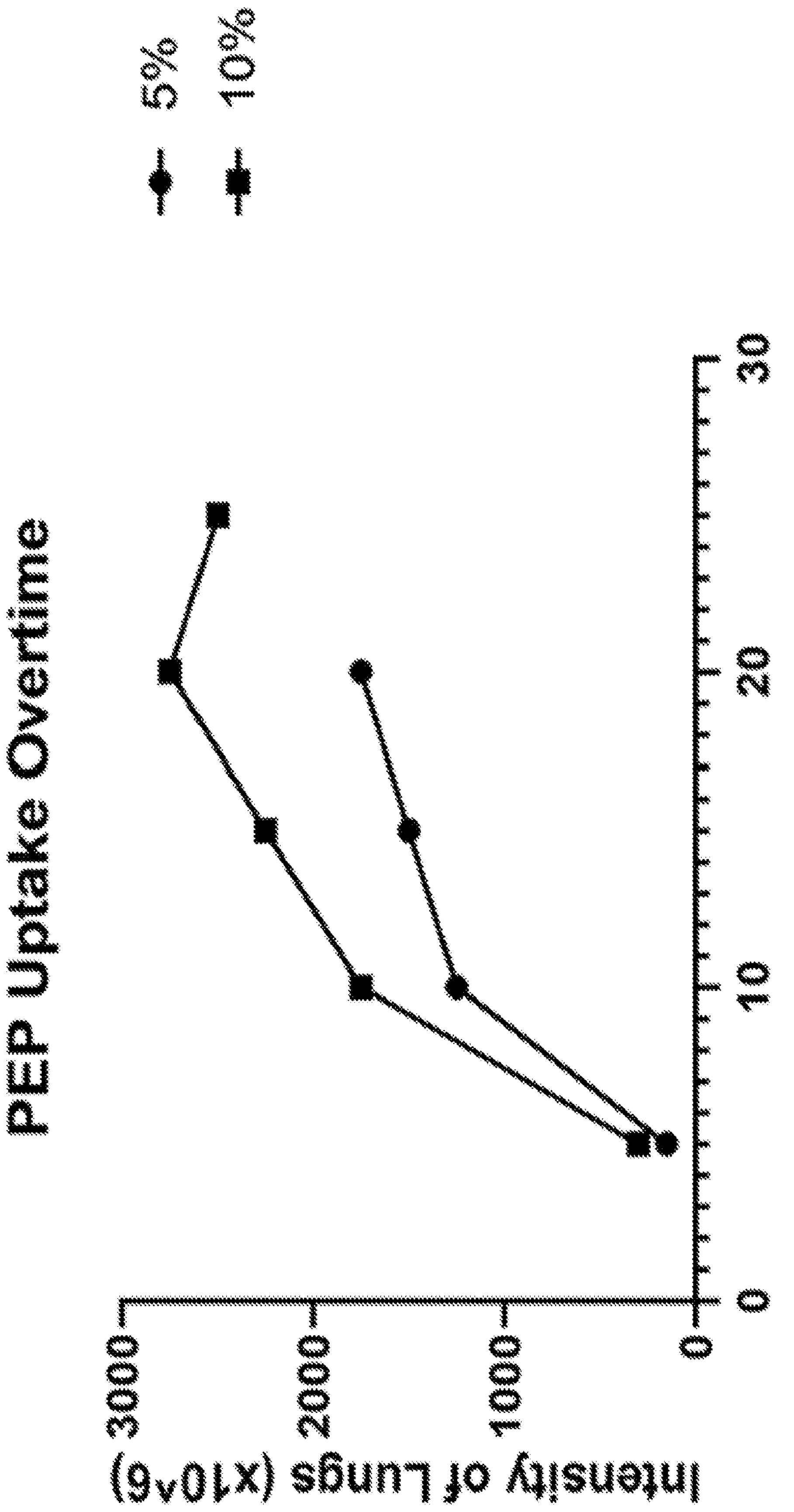
FIG. 17. A time course study to look at the DiR-labeled PEP accumulation in the lung via the route of nebulization. Dosages of 5% PEP or 10% PEP were administered for a period of five days, 10 days, 15 days, 20 days, or 25 days. PEP accumulation in the lungs reached plateau at 20 days. PEP was administered five minutes per day, five days per week. Each dose was administered as a PEP solution (approximately 0.6-0.8 ml) delivered via nebulization in five minutes.
Figure 18:
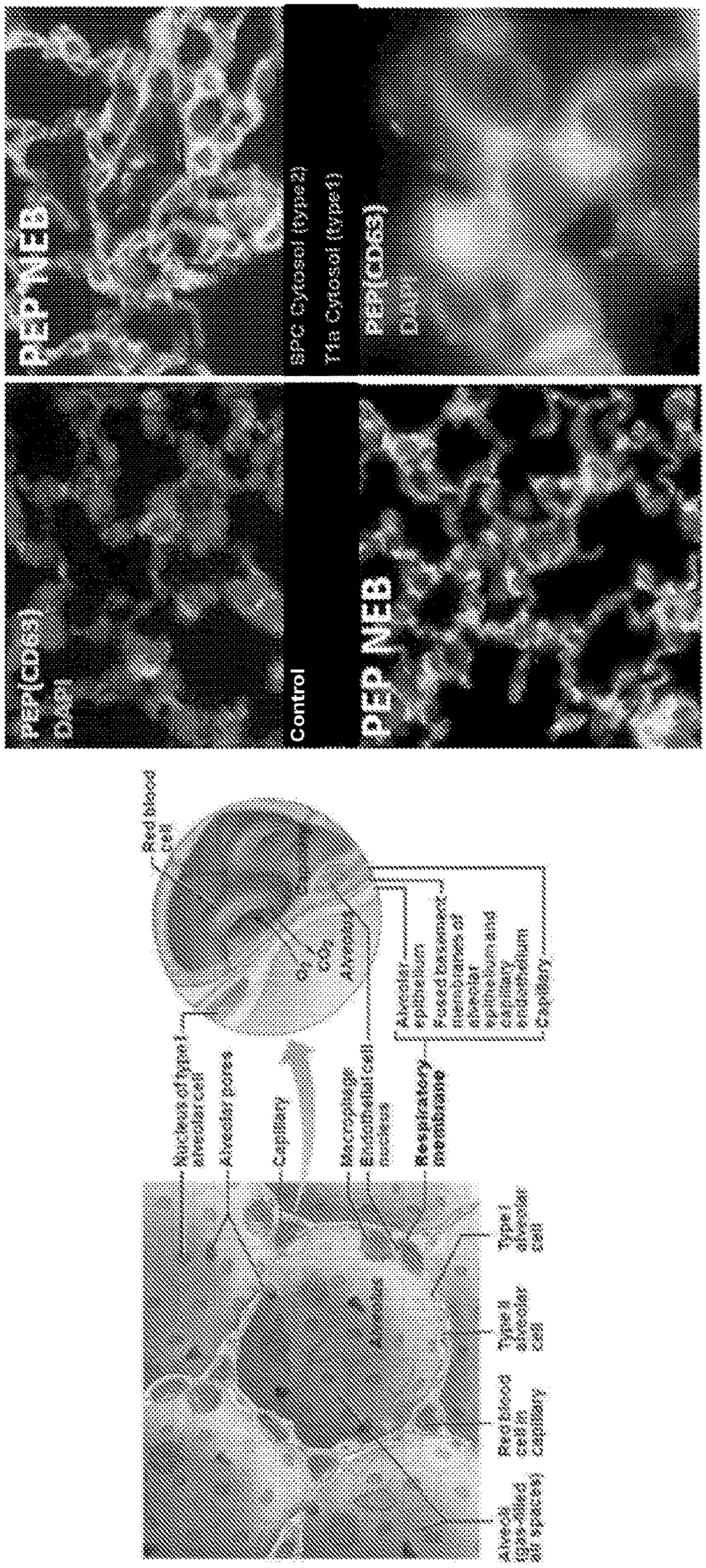
FIG. 18. PEP is detected in both type I alveolar cells and type II alveolar cells. (A) Schematic illustration of alveolar anatomy. (B) Immunohistochemistry: minimal endogenous CD63 staining (green) in a control murine lung. (C) Immunohistochemistry: CD63 staining (PEP-green) as well as staining for Surfactant protein C (SPC, red cytosolic staining) and T1 Alpha protein (red membrane staining). (D) Immunohistochemistry: intense CD63 staining (green) after nebulization with PEP for three days (five minutes per day with 20% PEP). (E) Immunohistochemistry: close up image (63× magnification) of (C). An antibody to CD63 was used to detect PEP; T1 alpha protein is a specific marker for type I alveolar cells; SPC is a marker for type II alveolar cells.

FIG. 13B illustrates the design of experiments to test whether PEP administered after cells are exposed to VSV-GFP can inhibit virus proliferation. FIG. 15 shows that PEP administered with or up to three hours after exposure to VSV-GFP caused a significant reduction in the amount of GFP-positive cells compared to the positive control, with profiles nearly identical in all cases to the negative control.

Exosomes and/or PEP can therefore be used to treat a viral infection. Viral infections treatable with PEP and/or exosomes include, but are not limited to, infections by viruses of the families Orthomyxoviridae, including but not limited to influenza A virus, influenza B virus, and influenza C virus; Flaviviridae, including but not limited to West Nile virus, Dengue virus, Zika virus, and hepatitis C virus; Rhabdoviridae, including but not limited to vesicular stomatitis virus, rabies virus, and Lagos bat virus; Filoviridae, including but not limited to Marburg virus and Ebola virus: Coronaviridae, including but not limited to severe acute respiratory syndrome coronavirus (SARS-CoV) and SARS-CoV-2 Retroviridae, including but not limited to human immunodeficiency virus (HIV)-1, Moloney leukaemia virus, and Jaagsiekte sheep retrovirus; Arenaviridae, including but not limited to Lassa virus, Machupo virus, lymphocytic choriomeningitis virus, and Lujo virus; Togaviridae, including but not limited to Semliki Forest virus; Bunyaviridae, including but not limited to La Crosse virus, Hantaan virus, Andes virus, Rift Valley fever virus, and Crimean-Congo haemorrhagic fever virus; and Reoviridae, including but not limited to reovirus.

Treating a viral infection can be prophylactic or, alternatively, can be initiated after the subject exhibits one or more symptoms or clinical signs of a condition caused by the viral infection. Treatment that is prophylactic—e.g., initiated before a subject manifests a symptom or clinical sign of the condition such as, for example, while an infection remains subclinical—is referred to herein as treatment of a subject that is "at risk" of having the condition. As used herein, the term "at risk" refers to a subject that may or may not actually possess the described risk. Thus, for example, a subject "at risk" of infectious condition is a subject present in an area where other individuals have been identified as having the infectious condition and/or is likely to be exposed to the infectious virus even if the subject has not yet manifested any detectable indication of infection by the virus and regardless of whether the subject may harbor a subclinical level of infection.

Accordingly, a composition that includes exosomes and/or PEP can be administered before, during, or after the subject first comes in contact with the infectious virus. Treatment initiated before the subject first comes in contact with the infectious virus may result in decreasing the likelihood that the subject experiences clinical evidence of the viral infection compared to a subject to which the composition is not administered, decreasing the severity of symptoms and/or clinical signs of the condition caused by the viral infection, and/or completely resolving the viral infection. Treatment initiated after the subject first comes in contact with the infectious virus may result in decreasing the severity of symptoms and/or clinical signs of the condition caused by the viral infection compared to a subject to which the composition is not administered, and/or completely resolving the viral infection.

Thus, the method includes administering an effective amount of the composition to a subject having, or at risk of having, a viral infection. In this aspect, an "effective amount" is an amount effective to reduce, limit progression, ameliorate, or resolve, to any extent, a symptom or clinical sign related to a condition caused by the viral infection.

PEP and/or exosomes may be formulated with a pharmaceutically acceptable carrier to form a pharmaceutical composition. As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with the PEP and/or exosomes without causing any undesirable biological effects or interacting in a deleterious manner with any of the other components of the pharmaceutical composition in which it is contained.

A pharmaceutical composition containing PEP and/or exosomes, whether intended for treating a condition caused by or associated with oxidative stress or a condition associated with or caused by a viral infection, may be formulated in a variety of forms adapted to a preferred route of administration. Thus, a pharmaceutical composition can be administered via known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical composition can be administered to a mucosal surface, such as by administration to, for example, the nasal or respiratory mucosa (e.g., by spray or aerosol). A pharmaceutical composition also can be administered via a sustained or delayed release.

Thus, a pharmaceutical composition may be provided in any suitable form including but not limited to a solution, a suspension, an emulsion, a spray, an aerosol, or any form of mixture. The pharmaceutical composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

A formulation may be conveniently presented in unit dosage form and may be prepared by methods well known in the art of pharmacy. Methods of preparing a composition with a pharmaceutically acceptable carrier include the step of bringing the PEP and/or exosomes into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The amount of PEP and/or exosomes administered can vary depending on various factors including, but not limited to, the content and/or source of the PEP and/or exosomes being administered, the weight, physical condition, and/or age of the subject, and/or the route of administration. Thus, the absolute weight of PEP and/or exosomes included in a given unit dosage form can vary widely, and depends upon factors such as the species, age, weight and physical condition of the subject, and/or the method of administration. Accordingly, it is not practical to set forth generally the amount that constitutes an amount of PEP and/or exosomes effective for all possible applications. Those of ordinary skill in the art, however, can readily determine the appropriate amount with due consideration of such factors.

In some embodiments, the method can include administering sufficient PEP and/or exosomes to provide a dose of, for example, from about a 0.01% solution to a 100% solution to the subject, although in some embodiments the methods may be performed by administering PEP and/or exosomes in a dose outside this range. As used herein, a 100% solution of PEP refers to PEP solubilized in 1 ml of a liquid carrier (e.g., water, phosphate buffered saline, serum free culture media, etc.). For comparison, a dose of 0.01% PEP is roughly equivalent to a standard dose of exosomes prepared using conventional methods of obtaining exosomes such as exosome isolation from cells in vitro using standard cell conditioned media.

In some embodiments, therefore, the method can include administering sufficient PEP and/or exosomes to provide a minimum dose of at least 0.01%, at least 0.05%, at least 0.1%, at least 0.25%, at least 0.5%, at least 1.0%, at least 2.0%, at least 3.0%, at least 4.0%, at least 5.0%, at least 6.0%, at least 7.0%, at least 8.0%, at least 9.0%, at least 10%, at least 15%, at least 20%, at least 25%, at least 30%, at least 35%, at least 40%, at least 45%, at least 50%, at least 60%, or at least 70%.

In some embodiments, the method can include administering sufficient PEP and/or exosomes to provide a maximum dose of no more than 100%, no more than 90%, no more than 80%, no more than 70%, no more than 60%, no more than 50%, no more than 40%, no more than 30%, no more than 20%, no more than 10%, no more than 9.0%, no more than 8.0%, no more than 7.0%, no more than 6.0%, no more than 5.0%, no more than 4.0%, no more than 3.0%, no more than 2.0%, no more than 1.0%, no more than 0.9%, no more than 0.8%, no more than 0.7%, no more than 0.6%, no more than 0.5%, no more than 0.4%, no more than 0.3%, no more than 0.2%, or no more than 0.1%.

In some embodiments, the method can include administering sufficient PEP and/or exosomes to provide a dose characterized by a range having endpoints defined by any a minimum dose identified above and any maximum dose that is greater than the minimum dose. For example, in some embodiments, the method can include administering sufficient PEP and/or exosomes to provide a dose of from 1% to 50% such as, for example, a dose of from 5% to 20%. In certain embodiments, the method can include administering sufficient PEP and/or exosomes to provide a dose that is equal to any minimum dose or any maximum dose listed above. Thus, for example, the method can involve administering a dose of 0.05%, 0.25%, 1.0%, 2.0%, 5.0%, 20%, 25%, 50%, 80%, or 100%.

In some embodiments, PEP and/or exosomes may be administered, for example, from a single dose to multiple administrations per week, although in some embodiments the method can be performed by administering PEP and/or exosomes at a frequency outside this range. When multiple administrations are used within a certain period, the amount of each administration may be the same or different. For example, a dose of 1 mg per day may be administered as a single administration of 1 mg, two administrations of 0.5 mg, or as a first administration of 0.75 mg followed by a second administration of 0.25 mg. Also, when multiple administrations are used within a certain period, the interval between administrations may be the same or be different.

In certain embodiments, PEP and/or exosomes may be administered from a one-time administration or from once per month to once per day to multiple times per day, depending on the application. For example, PEP and/or exosomes may be administered as a one-time treatment for acute myocardial infarction. In other embodiments, the PEP-exosomes may be administered multiple times in a day for wound healing or cosmetic uses.

In some embodiments, the methods can include administering a cocktail of exosomes and/or PEP that is prepared from a variety of cell types, each cell type having a unique antiviral protein profile. In this way, the exosome and/or PEP composition can provide a broader spectrum of antiviral activity than if the exosome and/or PEP composition is prepared from a single cell type.

EXAMPLES

Preparation of PEP

PEP preparation were prepared as previously described (International Publication No. WO 2019/118817 A1; U.S. Pat. No. 10,596,123 B2; U.S. Patent Application Publication No. US 2016/0324794 A1) and U.S. Patent Application Publication No. US 2021/0169812 A1.

Western Blot Analysis

PEP and other cell line pellets were reconstituted with lysis buffer containing 50 mmol/L NaCl, 50 mmol/L NaF, 50 mmol/L sodium pyrophosphate, 5 mmol/L EDTA, 5 mmol EGTA, 2 mmol/L $Na_3VO_4$, 1% Triton X-100, 0.5 mmol/L PMSF, 10 mmol/L HEPES, 10 ug/ml leupeptin at pH 7.4. Soluble protein extracts (20 μg per sample) were loaded onto 12.5% polyacrylamide gels (Bio-Rad Laboratories, Inc., Hercules, CA). Gels were then transferred to polyvinylidene difluoride (PVDF) membranes. Primary antibodies against various antigens were incubated overnight and subsequently probed with appropriate secondary antibodies for one hour and visualized using enhanced chemiluminescence.

NANOSIGHT Analysis of PEP

PEP exosome size and number was analyzed using a NANOSIGHT 300 particle analyzer (Malvern Panalytical Ltd., Salisbury, UK). PEP was reconstituted in 5 ml of water to yield a 20% PEP solution. This was further diluted 1:1000 before analysis. Each sample was analyzed three times and the average was taken.

Live Cell Imaging and Apoptosis Detection

Real time imaging of cells was performed using the INCUCYTE S3 imaging system (Essen Bioscience, Inc., Ann Arbor, MI) according to the manufacturer's directions. The Caspase 3/7 dye reagent was used according to manufacturer's guidelines (Essen Bioscience, Inc., Ann Arbor, MI)

DiR Labeling of PEP for XENOGEN Studies

For XENOGEN (Caliper Life Sciences, Inc., Hopkinton, MA) image analysis, PEP was labeled with the far red dye DiR (Thermo Fisher Scientific, Inc., Waltham, MA) according to manufacturer's guidelines. The near IR fluorescent, lipophilic carbocyanine $DiOC_{18}(7)$ ('DiR') is weakly fluorescent in water but highly fluorescent and quite photostable when incorporated into membranes. PEP was reconstituted with $dH_2O$ and filtered through a 0.20 m filter. After incubating with DiR dye at room temperature for 30 minutes on a rotator, the PEP-DiR solution was spun down at the maximum speed (14,800 rpm) in a temperature controlled countertop small centrifuge for 30 minutes and washed once with $dH_2O$.

Flow Cytometry

Cells were harvested and washed with PBS and FACS Buffer (1.8% BSA, 1 mm EDTA in PBS). Cells were resuspended in 100 μl of buffer and fixed with 2% paraformaldehyde prior to flow cytometric analysis.

In the preceding description and following claims, the term "and/or" means one or all of the listed elements or a combination of any two or more of the listed elements; the terms "comprises," "comprising," and variations thereof are to be construed as open ended i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of treating tissue damage caused by oxidative stress in a subject having, or at risk of having, tissue damage caused by oxidative stress, the method comprising:

administering to the subject a composition that includes exosomes comprising at least one antioxidant protein in an amount effective to reduce the likelihood or severity of tissue damage compared to a subject to whom the composition is not administered, the exosomes prepared by a process that comprises:

freezing material comprising cells comprising the exosomes under conditions effective to disrupt the cells but maintain the structure of the exosomes; and thawing the frozen material at a controlled rate of from 0.1° C. to 5° C. per minute.

2. The method of claim 1, wherein the antioxidant protein comprises catalase, heme oxygenase-1 (HO-1), Cu/Zn superoxide dismutase (SOD 1), Mn superoxide dismutase (SOD 2), or extracellular superoxide dismutase (SOD 3).

3. The method of claim 1, wherein the exosomes comprise catalase, heme oxygenase-1 (HO-1), Cu/Zn superoxide dismutase (SOD 1), Mn superoxide dismutase (SOD 2), and extracellular superoxide dismutase (SOD 3).

4. The method of claim 1, wherein the exosomes are provided in an amount effective to decrease apoptosis in cells of tissue that is oxidatively stressed.

5. The method of claim 1, wherein the exosomes have a mean diameter of 110 nanometers (nm)±30 nm.

* * * * *